(12) United States Patent
Kim et al.

(10) Patent No.: US 8,968,802 B2
(45) Date of Patent: Mar. 3, 2015

(54) COMPOSITION CONTAINING COLORED-BEAN EXTRACT

(75) Inventors: Jin Kwan Kim, Suwon-si (KR); Chae Wook Kim, Yongin-si (KR); Yeon Su Jeong, Yongin-si (KR); Jun Won Yun, Bucheon-si (KR); Kyung Min Lim, Hwaseong-si (KR); Yung Hyup Joo, Yongin-si (KR); Young Ho Park, Seoul (KR); Hyun Jung Shin, Seoul (KR)

(73) Assignee: Amorepacific Corporation (KR)

( * ) Notice: Subject to any disclaimer, the term of this patent is extended or adjusted under 35 U.S.C. 154(b) by 0 days.

(21) Appl. No.: 13/805,254

(22) PCT Filed: Jun. 17, 2011

(86) PCT No.: PCT/KR2011/004449
§ 371 (c)(1),
(2), (4) Date: Dec. 18, 2012

(87) PCT Pub. No.: WO2011/159133
PCT Pub. Date: Dec. 22, 2011

(65) Prior Publication Data
US 2013/0095197 A1   Apr. 18, 2013

(30) Foreign Application Priority Data
Jun. 18, 2010 (KR) .................. 10-2010-0058067

(51) Int. Cl.
*A61K 36/48* (2006.01)
*A61K 36/185* (2006.01)
(52) U.S. Cl.
CPC ...................... *A61K 36/48* (2013.01)
USPC ........................ 424/757; 424/725

(58) Field of Classification Search
CPC A61K 36/48; A61K 2035/124; A61K 48/005
USPC .................................. 424/757, 725
See application file for complete search history.

(56) References Cited

U.S. PATENT DOCUMENTS 7,238,379 B2 * 7/2007 Lang ........................ 426/542
2012/0070520 A1 * 3/2012 Shin et al. ................. 424/757

FOREIGN PATENT DOCUMENTS

JP         01-291761        11/1989
KR     10-2001-0074008       8/2001

OTHER PUBLICATIONS

Kwong, Dae Young et al., "A Study of Traditional Korean Soybeans for Development of Value Added Products", Research Paper, 2001.
Hae-Sook Oh et al., "Isoflavone Contents, Antioxidant and Fibrinolytic Activities of Some Commercial Cooking-with Rice Soybeans", Korean J. Food Sci., vol. 34, No. 3, pp. 498-504, 2002.
International Search Report—PCT/KR2011/0004449 dated Feb. 24, 2012.
Written Opinion—PCT/KR2011/004449 dated Feb. 24, 2012.

\* cited by examiner

*Primary Examiner* — Chris R Tate
*Assistant Examiner* — Randall Winston
(74) *Attorney, Agent, or Firm* — Cantor Colburn LLP (57) ABSTRACT

The present invention relates to an antithrombotic composition comprising a colored-bean extract or a fraction of the extract. The antithrombotic composition is highly useful for the treatment of diseases of the circulatory system, including cardiovascular disease, cerebrovascular disease, arteriosclerosis, hypertension and diabetes, which are caused by thrombosis.

5 Claims, 4 Drawing Sheets

1: 200 mg/kg of HP-20 resin 50% ethanol fraction of Seoritae (containing citric acid) extract
2: 200 mg/kg of HP-20 resin 50% ethanol fraction of field bean (containing citric acid) extract
3: 200 mg/kg of HP-20 resin 50% ethanol fraction of Seomoktae (containing citric acid) extract
4: 200 mg/kg of HP-20 resin 50% ethanol fraction of soybean (containing citric acid) extract

FIG.3

1: 200 mg/kg of 20% ethanol extract
   (containing citric acid) of field bean
2: 200 mg/kg of HP-20 resin 50% ethanol fraction
   of 20% ethanol extract (containing citric acid)
   of field bean
3: 200 mg/kg of HP-20 resin 50% ethanol fraction
   of 20% ethanol extract (containing no citric acid)
   of field bean

FIG.4

COMPOSITION CONTAINING COLORED-BEAN EXTRACT

TECHNICAL FIELD

The present invention relates to an antithrombotic composition containing, as an active ingredient, a colored-bean extract obtained using water, a $C_1$-$C_5$ alcohol or a mixture thereof and an organic acid, or a fraction of the extract

BACKGROUND ART

In recent years, the development of diseases of the circulatory system in the middle-aged and elderly groups, which are called adult diseases, has increased due to a change in dietary lifestyle and an increase in intrinsic and extrinsic stress, and this increase has become a serious problem. According to statistics provided by the Korean National Statistical Office in 2008, cerebrovascular diseases and heart diseases, including atherosclerosis, cerebral hemorrhage, stroke and cerebral infarction, are the first or second leading cause of death among death causes except for cancer. The major cause of these diseases is thrombus, and thrombosis is a pathology caused by excessive platelet aggregation. When blood vessels are damaged, platelets are activated by agonists such as collagen, thrombin, ADP (adenosine diphosphate) and the like, resulting in platelet adhesion, secretion and aggregation. This process plays an important role not only in hemostasis, but also in the development of diseases of the circulatory system, including thrombosis.

Coronary artery disease, a disease of the circulatory system, is known as one of causes of death, which are most frequent worldwide. Particularly, acute coronary syndrome is a coronary artery disease that is the direct cause of death. Acute coronary syndrome can be divided into unstable angina, non-ST-segment elevation myocardial infarction (NSTE; non Q-wave MI), and ST-elevation myocardial infarction (STE MI; Q-wave MI), and the former two also are collectively referred to as NSTE ACS (non-ST-elevation acute coronary syndrome), because treatment and prognosis are similar between the two. In chronic stable angina, ischemia is caused by a decrease in the effective diameter of coronary arteries due to atherosclerosis, but acute coronary syndrome has a mechanism different from that of chronic stable angina. Acute coronary syndrome occurs when blood flow is rapidly reduced or blocked by intracoronary acute thrombosis caused by the rupture or erosion of an atherosclerotic plaque.

More specifically, in acute coronary syndrome, the intravascular thrombotic process is the same as the process in which hemostasis occurs after traumatic vascular injury. In other words, when the rupture or erosion of a vulnerable atherosclerotic plaque occurs, connective tissue below endothelial cells is exposed to blood. Platelets in blood adhere to the exposed connective tissue (platelet adhesion), and the platelets are activated by mechanical and biochemical stimulation to secrete TxA2 (thromboxane A2), ADP (adenosine diphosphate), epinephrine and the like (platelet activation). These secreted substances activate GP IIb/IIIa receptor on the platelet surface, and the activated GP IIb/IIIa receptor causes platelets to aggregate by fibrinogen (platelet aggregation). Platelets are activated by many pathways, but are finally aggregated by fibrinogen through GP IIb/IIIa receptor, and thus this process is the final common pathway of platelet aggregation. Primarily produced thrombus is "white thrombus" rich in platelets and corresponds to the primary hemostasis of a hemostasis process.

The produced PRT (platelet-rich thrombus) is produced on the vascular wall of the injury portion of atherosclerotic plaques and usually does not completely occlude coronary arteries (Mural thrombus). This clinically corresponds to NTSE ACS. On PRT (platelet-rich thrombus), thrombin (factor IIa) is produced by activation of coagulation and chain reactions. Thrombin activates fibrinogen to fibrin, and activated fibrin forms a meshwork while a thrombus containing blood cells such as red blood cells is formed. The formed thrombus is "red thrombus" and corresponds to the secondary hemostasis of the hemostasis process. Thrombosis/thrombolysis balance is continued toward thrombolysis production, blood vessels are completely occluded, resulting in STE MI.

Antithrombotic drugs can be divided into anti-platelet agents for inhibiting platelets which are involved in primary hemostasis, and anticoagulants for inhibiting coagulation in secondary hemostasis. Anti-platelet agents include aspirin which inhibits TxA2 production, clopidogrel and ticlopidine, which are ADP receptor blockers, abciximab that is a GP IIb/IIIa receptor blocker, and the like. In addition, theopylline, molsidomine, verapamil, nifedipine, nitroglycerine and the like are known to promote of cAMP and cGMP, which inhibit the recruitment of $Ca^{2+}$. Anticoagulants include heparin that activates antithrombin III to degrade thrombin, the direct thrombin inhibitor (DTI) hirudin, the vitamin K antagonist warfarin and so on. However, the above-mentioned drugs can cause various side effects, including excessive inhibition of hemostasis in the human body, sterility, and disorders of the digestive system. Thus, there is a need to develop an agent, which significantly reduces the side effects of antithrombotic drugs and, at the same time, is safe.

DISCLOSURE

Technical Problem

One aspect of the present invention is to provide a composition having an antithrombotic effect.

Another aspect of the present invention is to provide a pharmaceutical composition or health food composition having an antithrombotic effect

Technical Solution

One aspect of the present invention provides a composition containing, as an active ingredient, a colored-bean extract obtained using water, a $C_1$-$C_5$ alcohol or a mixture thereof and an organic acid, or a fraction of the extract

Advantageous Effects

A composition according to one aspect of the present invention has an excellent antithrombotic effect, comprises a natural substance having no side effect and can be variously used in the pharmaceutical and health food fields.

MODE FOR INVENTION

Previous studies on beans were conducted in order to isolate and purify pharmacologically active ingredients from beans, and studies on the medical use of beans themselves are still insufficient. In addition, beans have been extracted using extraction methods employing high-concentration organic solvents, which are extraction methods commonly used to extract natural materials.

Bean extracts contain several unknown components in addition to identified components, and some of these components may exhibit pharmacological effects beneficial to the human body. In addition, useful components of beans can also not be extracted by an extraction method using a high-concentration organic solvent. Unlike extraction methods that are generally used to natural materials and medicinal herbs, the present inventors have obtained an extract from beans using water or a low-concentration organic solvent as an extraction solvent, and have found that a fraction obtained by fractionating the obtained bean extract with resin exhibits potent antithrombotic effects.

A composition according to one aspect of the present invention is characterized in that it contains a fraction of a bean extract obtained using water or a low-concentration organic solvent and an organic acid. A composition according to one aspect of the present invention may be an antithrombotic composition containing a colored-color extract obtained using water, a $C_1$-$C_5$ alcohol or a mixture thereof and an organic acid. A composition according to another aspect of the present invention may be an antithrombotic composition containing a fraction of a colored-color extract obtained using water, a $C_1$-$C_5$ alcohol or a mixture thereof and an organic acid.

In one embodiment of the present invention, the organic acid may be any one or more selected from the group consisting of citric acid, acetic acid, butyric acid, palmitic acid, oxalic acid, tartaric acid, carboxylic acid and sulfonic acid. More specifically, the organic acid may be citric acid. When the organic acid together with the low-concentration organic solvent is used to extract active ingredients from colored beans, the efficiency of extraction from the beans can be increased, and selectivity to the active ingredients can be increased.

In one embodiment of the present invention, the organic solvent is not specifically limited and may be a $C_1$-$C_5$ lower alcohol. The $C_1$-$C_5$ lower alcohol may be, for example, any one or a mixture of two or more selected from the group consisting of methanol, ethanol, isopropanol, n-propyl alcohol, n-butanol and isobutanol. Specifically, the $C_1$-$C_5$ lower alcohol may be ethanol.

In another embodiment of the present invention, the concentration of the $C_1$-$C_5$ alcohol is 1-70% (v/v), specifically 1-40% (v/v), more specifically 5-25% (v/v), and even more specifically 7-20% (v/v). For example, the solvent may be 5-25% (v/v) ethanol, and more specifically 10% or 20% (v/v) ethanol.

In the present invention, beans are extracted using water or a low-concentration lower alcohol and an organic acid. The present inventors have conducted various studies and repeated tests and, as a result, have found that a colored-bean extract obtained using a lower alcohol, for example, ethanol, particularly low-concentration ethanol, among a variety of organic solvents, together with an organic acid, is effective in improving blood circulation and preventing and treating obesity and diabetes and has excellent effects on the prevention and treatment of hyperlipidemia, thereby completing the present invention.

In one embodiment of the present invention, the colored-bean extract is an extract obtained using water, a $C_1$-$C_5$ alcohol or a mixture thereof and an organic acid, and a fraction of the extract is either a fraction separating the colored-bean extract by resin or a fraction obtained by fractionating the colored-bean extract with butanol. The resin fraction is, for example, a fraction obtained by fractionation using a synthetic adsorbent column including a polymer of benzene and polystyrene, and specifically a HP-20 resin fraction. The present inventors performed a test for extracting various fractions from a colored-bean extract obtained using low-concentration ethanol as a typical example. As a result, it was found that a HP-20 resin fraction or a butanol fraction has excellent antithrombotic effects compared to a water fraction.

As used herein, the term "colored bean" is meant to include beans whose husks have deep colors, including black, red, yellow and green. The colored bean may be any one or more selected from the group consisting of Seoritae (*Glycine max* MERR), Seomoktae (*Rhynchosia Nolubilis*), blue bean (*Glycine max* MERR), yellow bean (*Glycine max* MERR), field bean (*Phaseolus vulgaris* L.), kidney bean (*Phaseolus vulgaris*), pinto bean (*Phaseolus vulgaris* L.), small red bean (*Vigna angularis*), small black bean (*Phaseolus angularis* W.F. WIGHT.), sprouting bean (*Glycine max* (L.) Merr.), soybean (*Glycine max*), black soybean (*Glycine max*(L.) Merr.). In one embodiment of the present invention, the colored bean may be a field bean. The colored bean can be named in various manner ways depending on regions, classification, random talk and the like. As used herein, the term "colored-bean extract" refers collectively to substances extracted from colored beans by various extraction processes and includes, for example, substances extracted using water or an organic solvent. The extract may include various fractions (e.g., HP-20 resin fraction).

A composition containing the colored-bean extract fraction according to the present invention has the effect of inhibiting platelet aggregation to inhibit thrombosis, and has the effect of inhibiting vasoconstriction to induce vascular relaxation. Thanks to such effects, the composition of the present invention is effective in improving blood circulation and can be effectively used for the prevention or treatment of obesity, diabetes and hyperlipidemia.

One aspect of the present invention provides a pharmaceutical composition comprising the above-described composition as an active ingredient. In one embodiment of the present invention, the pharmaceutical composition may be a composition for the prevention, alleviation or treatment of vascular diseases. The pharmaceutical composition comprising the composition according to the present invention has the effect of preventing thrombosis, inhibiting vasoconstriction and suppressing cholesterol. Specifically, the pharmaceutical composition may be a pharmaceutical composition for improving blood circulation by antithrombotic activity and may be a pharmaceutical composition for the alleviation or treatment of vascular diseases, including obesity, diabetes and hyperlipidemia. Examples of the vascular diseases include obesity, diabetes, stroke, cerebral hemorrhage, arteriosclerosis, angina, myocardial infarction, hypertension, anemia, migraine or hyperlipidemia.

When the composition according to the present invention is applied to medical drugs, it can be formulated in liquid, semi-solid or solid forms for oral or parenteral administration using conventional inorganic or inorganic carriers.

Examples of formulations for oral administration include tablets, pills, granules, soft or hard capsules, powders, fine granules, emulsions, syrups, pellets and the like. Examples for formulations for parenteral administration include injectable solutions, drops, ointments, lotions, sprays, suspensions, suppositories and the like. The active ingredient of the present invention can be easily formulated according to conventional methods, and surfactants, excipients, colorants, flavoring agents, preservatives, stabilizers, buffers, suspending agents or other conventional additives can be suitably used for the formulation.

The pharmaceutical composition according to the present invention may be administered orally, parenterally, intrarectally, topically, transdermally, intravenously, intramuscularly, intraperitoneally or subcutaneously.

In addition, the dose of the active ingredient will vary depending on various factors, including the age, sex and weight of the subject to be treated, the particular disease or physiological condition to be treated, the severity of the physiological condition, the route of administration, and the physician's judgment. The determination of the dose based on such factors is within the level of those skilled in the art. The active ingredient may generally be administered at a dose of 0.001 mg/kg/day to 2000 mg/kg/day, and specifically 0.5 mg/kg/day to 1500 mg/kg/day, but is not limited thereto.

One aspect of the present invention provides a food additive, functional food or health food composition comprising the composition of the present invention as an active ingredient. In one embodiment of the present invention, the food additive, functional food or health food composition comprising the composition of the present invention as an active ingredient may be a composition for improving blood circulation and may be a composition for preventing or alleviating vascular diseases, including obesity, diabetes or hyperlipidemia. Examples of the vascular diseases include obesity, diabetes, stroke, cerebral hemorrhage, arteriosclerosis, angina, myocardial infarction, hypertension, anemia, migraine or hyperlipidemia.

Examples of the food additive or functional food comprising the composition of the present invention include fermented milk, cheese, yogurt, juice, probiotics, health supplement foods, and so on.

In one embodiment of the present invention, the composition may contain other components which can improve the effects of the present invention, as long as such components do not impair the effects of the present invention. For example, the composition of the present invention may further comprise additives, including fragrance, pigments, bactericides, antioxidants, preservatives, moisturizing agents, thickeners, inorganic salts, emulsifiers and synthetic polymers. In addition, the composition of the present invention may further comprise auxiliary components, including water-soluble vitamins, oil-soluble vitamins, polymer peptides, polysaccharides and seaweed extracts. The above components can be suitably selected without difficulty by those skilled in the art depending on the formulation or intended use of the composition and may be added in an amount selected within the range that does not impair the object and effect of the present invention. For example, the above components may be added in an amount of 0.01-5 wt %, and specifically 0.01-3 wt %, based on the total weight of the composition.

The composition of the present invention may be formulated in various forms, including solutions, emulsions, viscose mixtures, tablets, and powders, which can be administered by various methods, including sample drinking, injection, spraying or squeezing.

Hereinafter, the present invention will be described in further detail with reference to examples and test examples. It is to be understood, however, that these examples and test examples are for illustrative purposes and are not intended to limit the scope of the present invention.

Example 1

Preparation of Seoritae Extract Using 20% Ethanol and Organic Acid 1 kg of dried Seoritae were immersed in 5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 2

Preparation of Seomoktae Extract Using 20% ethanol and Organic Acid 1 kg of dried Seomoktae were immersed in 5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 3

Preparation of Kidney Bean Extract Using 20% Ethanol and Organic Acid 300 g of dried kidney beans were immersed in 1.5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 4

Preparation of Pinto Bean extract Using 20% Ethanol and Organic Acid 300 g of dried pinto beans were immersed in 1.5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 5

Preparation of Sprouting Bean Extract Using 20% Ethanol and Organic Acid 300 g of dried sprouting beans were immersed in 1.5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 6

Preparation of Yellow Bean extract Using 20% Ethanol and Organic Acid 300 g of dried yellow beans were immersed in 1.5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 7

Preparation of Blue Bean Extract Using 20% Ethanol and Organic Acid 300 g of dried blue beans were immersed in 1.5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 8

Preparation of Field Bean Extract Using 20% Ethanol and Organic Acid 1 kg of dried field beans were immersed in 5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 9

Preparation of Soybean Extract Using 20% Ethanol and Organic Acid 1 kg of dried soybeans were immersed in 5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 10

Preparation of Small Black Bean Extract Using 20% Ethanol and Organic Acid 300 g of dried small black beans were immersed in 5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 11

Preparation of Small Red Bean Extract Using 20% Ethanol and Organic Acid 300 g of dried small red beans were immersed in 5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 12

Preparation of Black Soybean Extract Using 20% Ethanol and Organic Acid 300 g of dried black soybeans were immersed in 5 L of 20% ethanol aqueous solution containing 1% citric acid and were extracted under reflux at 60° C. for 3 hours, and the extract was allowed to stand at room temperature for a predetermined time. Then, the extract was filtered, concentrated under reduced pressure and freeze-dried, thereby preparing a powder sample (yield: 3-15%). The prepared powder was stored at low temperature until use.

Example 13

Separation of Seoritae Bean Extract by HP-20 Resin 1 kg of dried Seoritae beans were immersed in 5 L of 20% ethanol solution containing 1% citric acid and were extracted under reflux at 60° C. for 3 hours, and the extract was allowed to stand at room temperature for a predetermined time. Then, the extract was filtered, concentrated under reduced pressure, and freeze-dried, thereby preparing a 20% ethanol extract sample. Using the hydrophobic resin DIAION HP-20 (SUPELCO), a resin fraction was obtained from the 20% ethanol organic acid extract of Seoritae beans in the following manner.

For separation by HP-20 resin, HP-20 resin was packed into a column to a length of 30 cm, and then washed twice with 500 ml of ethanol, twice with 500 ml of 50% ethanol, and twice with 500 ml of distilled water. 6 g of the 20% ethanol organic acid extract of Seoritae beans was dissolved in water and added to the HP-20 resin-packed column, and 750 ml of distilled water, 750 ml of 50% ethanol and 500 ml of ethanol were sequentially introduced into the column while each of the solvents discharged from the column was received in 250-ml Erlenmeyer flasks. Each of the discharged solvents was concentrated under reduced pressure and freeze-dried, thereby obtaining fraction samples.

Example 14

Separation of Field Bean Extract by HP-20 Resin 1 kg of dried field beans were immersed in 5 L of 20% ethanol solution containing 1% citric acid and were extracted under reflux at 60° C. for 3 hours, and the extract was allowed to stand at room temperature for a predetermined time. Then, the extract was filtered, concentrated under reduced pressure, and freeze-dried, thereby preparing a 20% ethanol organic extract sample. Using the hydrophobic resin DIAION HP-20 (SUPELCO), a resin fraction was obtained from the 20% ethanol organic acid extract of field beans in the following manner.

For separation by HP-20 resin, HP-20 resin was packed into a column to a length of 30 cm, and then washed twice with 500 ml of ethanol, twice with 500 ml of 50% ethanol, and twice with 500 ml of distilled water. 6 g of the 20% ethanol organic acid extract of field beans was dissolved in water and added to the HP-20 resin-packed column, and 750 ml of distilled water, 750 ml of 50% ethanol and 500 ml of ethanol were sequentially introduced into the column while each of the solvents discharged from the column was received in 250-ml Erlenmeyer flasks. Each of the discharged solvents was concentrated under reduced pressure and freeze-dried, thereby obtaining fraction samples.

Example 15

Separation of Kidney Bean Extract by HP-20 Resin 1 kg of dried field beans were immersed in 5 L of 20% ethanol solution containing 1% citric acid and were extracted under reflux at 60° C. for 3 hours, and the extract was allowed to stand at room temperature for a predetermined time. Then, the extract was filtered, concentrated under reduced pressure, and freeze-dried, thereby preparing a 20% ethanol organic acid extract sample. Using the hydrophobic resin DIAION HP-20 (SUPELCO), a resin fraction was obtained from the 20% ethanol organic acid extract of kidney beans in the following manner.

For separation by HP-20 resin, HP-20 resin was packed into a column to a length of 30 cm, and then washed twice with 500 ml of ethanol, twice with 500 ml of 50% ethanol, and twice with 500 ml of distilled water. 6 g of the 20% ethanol organic acid extract of kidney beans was dissolved in water and added to the HP-20 resin-packed column, and 750 ml of distilled water, 750 ml of 50% ethanol and 500 ml of ethanol were sequentially introduced into the column while each of the solvents discharged from the column was received in 250-ml Erlenmeyer flasks. Each of the discharged solvents was concentrated under reduced pressure and freeze-dried, thereby obtaining fraction samples.

Example 16

Separation of Soybean Extract by HP-20 Resin 1 kg of dried field beans were immersed in 5 L of 20% ethanol solution containing 1% citric acid and were extracted under reflux at 60° C. for 3 hours, and the extract was allowed to stand at room temperature for a predetermined time. Then, the extract was filtered, concentrated under reduced pressure, and freeze-dried, thereby preparing a 20% ethanol organic acid extract sample. Using the hydrophobic resin DIAION HP-20 (SUPELCO), a resin fraction was obtained from the 20% ethanol organic acid extract of soybeans in the following manner.

For separation by HP-20 resin, HP-20 resin was packed into a column to a length of 30 cm, and then washed twice with 500 ml of ethanol, twice with 500 ml of 50% ethanol, and twice with 500 ml of distilled water. 6 g of the 20% ethanol organic acid extract of soybeans was dissolved in water and added to the HP-20 resin-packed column, and 750 ml of distilled water, 750 ml of 50% ethanol and 500 ml of ethanol were sequentially introduced into the column while each of the solvents discharged from the column was received in 250-ml Erlenmeyer flasks. Each of the discharged solvents was concentrated under reduced pressure and freeze-dried, thereby obtaining fraction samples.

Example 17

Separation of Seomoktae Bean Extract by HP-20 Resin 1 kg of dried field beans were immersed in 5 L of 20% ethanol solution containing 1% citric acid and were extracted under reflux at 60° C. for 3 hours, and the extract was allowed to stand at room temperature for a predetermined time. Then, the extract was filtered, concentrated under reduced pressure, and freeze-dried, thereby preparing a 20% ethanol organic acid extract sample. Using the hydrophobic resin DIAION HP-20 (SUPELCO), a resin fraction was obtained from the 20% ethanol organic acid extract of Seomoktae beans in the following manner.

For separation by HP-20 resin, HP-20 resin was packed into a column to a length of 30 cm, and then washed twice with 500 ml of ethanol, twice with 500 ml of 50% ethanol, and twice with 500 ml of distilled water. 6 g of the 20% ethanol organic acid extract of Seomoktae beans was dissolved in water and added to the HP-20 resin-packed column, and 750 ml of distilled water, 750 ml of 50% ethanol and 500 ml of ethanol were sequentially introduced into the column while each of the solvents discharged from the column was received in 250-ml Erlenmeyer flasks. Each of the discharged solvents was concentrated under reduced pressure and freeze-dried, thereby obtaining fraction samples.

Example 18

Solvent Fractionation of Field Bean Extract 10.18 g of the 20% ethanol organic acid extract of field beans, obtained in Example 8, was dissolved in 100 ml of distilled water and then extracted twice with 100 ml of ethyl acetate (EtOAc) using a separatory funnel. The remaining water layer was extracted twice with 100 ml of n-butanol (n-BuOH). Each of the obtained ethyl acetate (EtOAc), n-butanol (n-BuOH) and water layers was concentrated under reduced pressure and freeze-dried, thereby preparing samples. The yield was 4.62% for the ethyl acetate (EtOAc) layer, 6.58% for the n-butanol (n-BuOH) layer and 8.88% for the water layer, and the samples were cold-stored until use.

Test Example 1

Observation of Inhibition of Human Platelet Aggregation Induced by Collagen

In order to examine the change in activity of an extract with a change in the ethanol content of an extraction solvent, the following test was performed using field bean extracts obtained using extraction solvents having varying water or ethanol contents.

To separate human platelet-rich plasma (PRP), 3.2% sodium citrate was used as an anti-coagulating agent, and blood was collected from the veins of healthy men who have not taken any medicine for 2 weeks or more. 150 g of the collected blood was centrifuged for 15 minutes, the supernatant (PRP) was collected, and the residue was centrifuged to separate platelet-poor plasma (PPP). Platelets in the collected PRP were counted using a cell counter, and PRP was diluted with PPP to a concentration of $3 \times 10^8$ platelets/ml and used in the test.

Platelet aggregation activity was determined based on the change in absorbance using a lumi-aggregometer (Chrono-Log Co., USA). PRP was pre-incubated in a thermomixer at 37° C. for 2 minutes, and a field bean extract was added to the pre-incubated PRP at a concentration of 200 μg/ml and incubated for 7 minutes. 500 μl of the incubated PRP was added to and incubated in a silicone-coated cuvette for platelet aggregation and incubated for 3 minutes. Then, collagen as a platelet aggregation inducer was added at the minimum concentration of 1-3 μg/ml, which cause the maximum platelet aggregation, after which the reaction was observed for 6 minutes. The results of the observation are expressed in Table 1 below as plate aggregation inhibitory rates (%) relative to the platelet aggregation inhibitory rate (0%) of the control group treated with collagen alone.

TABLE 1

| Sample | Inhibition rate (%) |
|---|---|
| Water organic acid extract | 39.3 |
| 10% ethanol organic acid extract | 53.5 |
| 20% ethanol organic acid extract | 63.7 |
| 30% ethanol organic acid extract | 17.3 |
| 40% ethanol organic acid extract | 9.3 |
| 50% ethanol organic acid extract | 6.0 |
| 70% ethanol organic acid extract | 1.0 |

As can be seen in Table 1 above, the water, 10% and 20% ethanol extracts showed excellent effects on the inhibition of platelet aggregation compared to other extracts. Among them, the 20% ethanol extract which showed the highest effect on the inhibition of platelet aggregation was used in subsequent tests.

Test Example 2

Observation of Human Platelet Aggregation Inhibitory Effects of Various Beans

Under the same conditions as the preparation of the 20% ethanol organic acid extract shown to have the highest activity, the following test performed in order to examine whether various beans have platelet aggregation inhibitory effects. The beans used in the test were all produced in Korea.

The test was performed for small black beans, soybeans, Seoritaes, Seomoktaes, field beans, kidney beans, pinto beans, small red beans, blue beans, sprouting beans, yellow beans, and black soybeans. The beans were extracted according to the method described in the Examples. In addition, in order to observe the platelet aggregation inhibitory effects of the extracts, the test was performed using 200 μg/ml of 20% ethanol organic acid extract of each bean under the same conditions as those of Test Example 1. The results of the test are expressed in Table 2 below as platelet aggregation inhibitory rates (%).

TABLE 2

| Sample | Inhibition rate (%) |
|---|---|
| Small black bean | 5.0 |
| Soybean | 32.3 |
| Seomoktae | 27.7 |
| Seoritae | 12.0 |
| Field bean | 63.7 |
| Kidney bean | 24.0 |
| Pinto bean | 15.0 |
| Small red bean | 7.0 |
| Blue bean | 12.5 |
| Sprouting bean | 25.0 |
| Yellow bean | 7.0 |
| Black soybean | 11.5 |

As can be seen in Table 2 above, the extract of field beans had the highest effect on the inhibition of platelet aggregation.

Test Example 3

Platelet Aggregation Inhibitory Activity of Fraction of Each Bean Extract

Under the same conditions as the preparation of the 20% ethanol organic acid extract shown to have the highest activity, extracts of various beans were fractionated with HP-20 resin according to the method described in the Examples.

Under the same conditions as those of Test Example 1, a test was performed using 200 μg/ml of a water fraction (hereinafter referred to as "HP-20 resin water fraction) and a 50% ethanol fraction (hereinafter referred to as "HP-20 resin 50% ethanol fraction), which were obtained by fractionating the 20% ethanol organic acid extract of each bean. The results of the test are expressed in Table 3 below as platelet aggregation inhibitory rates (%).

TABLE 3

| | 20% ethanol organic acid extract before fractionation with HP-20 resin | After fractionation with HP-20 resin | |
|---|---|---|---|
| | | Water fraction | 50% ethanol fraction |
| | 200 μg/ml | 200 μg/ml | 100 μg/ml | 200 μg/ml |
| Soybean | 32.3 | 4.7 | 43.7 | 85.7 |
| Seomoktae | 27.7 | 2.7 | 61.7 | 93.0 |
| Seoritae | 12.0 | 5.0 | 19.3 | 61.3 |
| Field bean | 63.7 | 9.3 | 49.5 | 94.3 |
| Kidney bean | 24.0 | 13.0 | 32.0 | 67.5 |

Figure 1:
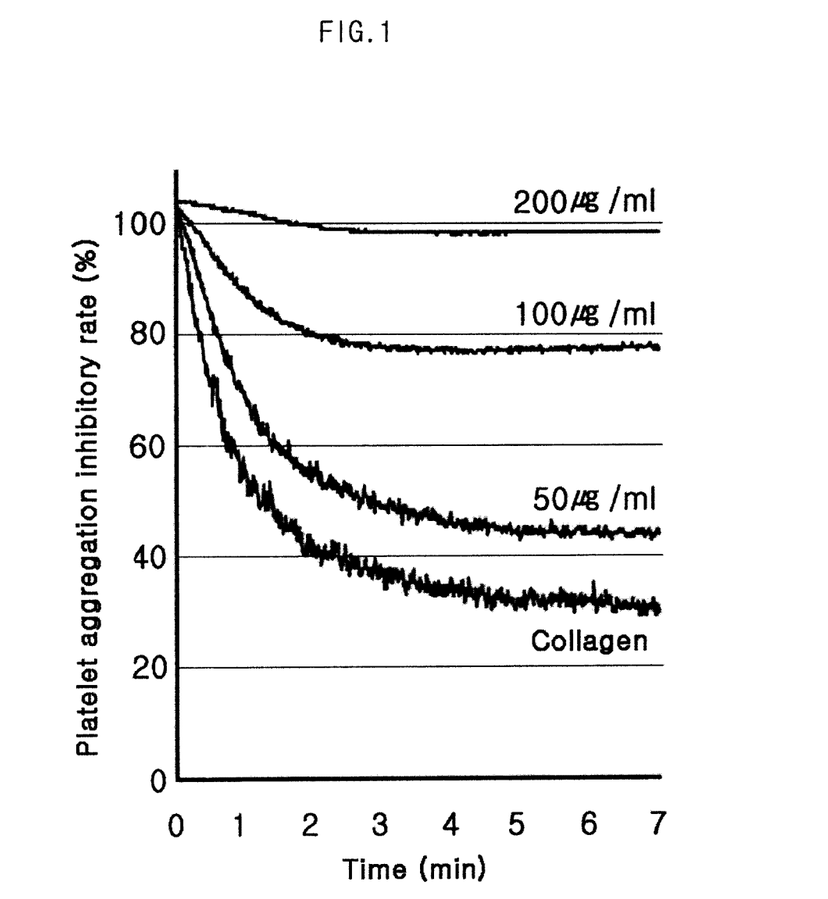
FIG. 1 is a graph showing the platelet aggregation inhibitory effect as a function of the concentration of a 50% ethanol fraction obtained by fractionating a 20% ethanol organic acid extract of field beans with HP-20 resin.

As can be seen in Table 3 above, in the case of all the beans, the HP-20 resin 50% ethanol extract showed a significantly excellent effect on the inhibition of platelet aggregation compared to the H-20 resin water fraction, and the active ingredients were mostly concentrated on the HP-20 resin 50% ethanol fraction. This activity was concentration-dependent, and FIG. 1 shows the platelet aggregation inhibitory effects of the H-20 resin 50% ethanol fraction of the field bean extract.

Test Example 4

Observation of Specific Inhibition of Activity of Each Platelet Aggregation-Stimulating Source In order to examine whether the HP-20 resin 50% ethanol fraction of the 20% ethanol extract of each bean, which has showed the highest inhibitory activity, specifically inhibits each of platelet aggregation-stimulating sources, the following test was carried out.

When a blood vessel is damaged, an endothelial cell layer in the damaged site is broken, the blood vessel is exposed to collagen, and ADP (adenosine diphosphate) and thrombin are secreted from platelets. These substances are known to stimulate platelet aggregation. Thus, in order to examine whether the HP-20 resin ethanol 50% ethanol fractions specifically inhibit platelet aggregation activities caused by ADP and thrombin, a test was performed in the same manner as Test Example, except that ADP and thrombin stimulations were applied instead of collagen stimulation. The results of the test are expressed in Table 4 below as platelet aggregation inhibitory rates (%).

TABLE 4

|  | ADP | Thrombin |
|---|---|---|
| Soybean | 66.3 | 45.3 |
| Seomolctae | 79.3 | 62.7 |
| Seoritae | 44.0 | 34.3 |
| Field bean | 92.0 | 74.3 |
| Kidney bean | 74.0 | 46.0 |

As can be seen in Table 4, the HP-20 resin 50% ethanol fractions showed inhibitory effects not only on platelet aggregation induced by collagen, but also on platelet aggregation induced by other stimulants such as ADP and thrombin. Particularly, the HP-20 resin 50% ethanol fractions of the extracts of Seomoktae and filed beans had better effects on the inhibition of plate aggregation.

Test Example 5

Observation of Human Platelet Aggregation Inhibitory Effect of Each Fraction of Field Bean Extract In order to identify a solvent fraction showing the highest activity among solvent fractions of the field bean extract which has showed the highest activity among the bean extracts, the following test was performed.

First, ethyl acetate, butanol and water fractions of the field bean extract were prepared according to the method of Example 18. In order to examine the platelet aggregation inhibitory effect of each of the fractions, a test was performed using 200 μg/ml of each fraction under the same conditions as those of Test Example 1. The results of the test are expressed in Table 5 below as platelet aggregation inhibitory rates (%).

TABLE 5

|  | Ethylacetate fraction | Butanol fraction | Water fraction |
|---|---|---|---|
| Field bean | 23.0 | 86.5 | 23.5 |

As can be seen in Table 5 above, the platelet aggregation activity was the highest in the butanol fraction and was similar between the ethylacetate fraction and the water fraction. This suggests that the platelet aggregation inhibitory effect of the low-concentration ethanol extract of field beans is attributable to the active ingredient contained in the butanol fraction.

Test Example 6

Observation Effect of Butanol Fraction on Inhibition of Activity of Each of Platelet Aggregation-Stimulating Sources In order to examine whether the butanol fraction of the field bean extract specifically inhibits the activity of each of platelet aggregation-stimulating sources, a test was performed for the stimulation of ADP and thrombin in the same manner as Test Example 4. In the test, the butanol fraction was used at a concentration of 200 μg/ml. The results of the test are expressed in Table 5 below as platelet aggregation inhibitory rates (%).

TABLE 6

| ADP | Thrombin |
|---|---|
| 66.0 | 63.5 |

As can be seen in Table 6 above, the butanol fraction of the field bean extract inhibited platelet aggregation induced not only by collagen, but also by ADP and thrombin.

Test Example 7

Observation of Inhibitory Effects of Fractions on Secretion of Activator Substance After Platelet Aggregation In order to examine the inhibitory effect of the HP-20 resin 50% ethanol fraction of each bean extract on the production of thromboxane after platelet aggregation, 400 μg/ml of each fraction sample was added to PRP obtained in Test Example 1 and was incubated at 37° C. for 10 minutes, after which 5 μg/ml of collagen was added thereto and allowed to react for 6 minutes. 2 mM EDTA and 50 μM indomethacin were added thereto to stop the reaction. The resulting reaction solution was centrifuged at 2000×g for 20 minutes, and the supernatant was taken. The amount of thromboxane in the supernatant was quantified by an enzyme immunoassay. The results of the test are expressed in Table 7 below as thromboxane production inhibitory rates (%).

TABLE 7

|  | Inhibition rate (%) |
|---|---|
| Soybean | 36.9 |
| Seomoktae | 52.7 |
| Seoritae | 24.5 |
| Field bean | 44.8 |
| Kidney bean | 36.7 |
| Butanol fraction of field bean | 40.5 |

As can be seen in Table 7 above, the HP-20 resin 50% ethanol fraction of each bean and the butanol fraction of each bean inhibited the production of thromboxane after plate aggregation.

Test Example 8

Observation of Inhibitory Effects on Vinous Thrombosis in SD Rats

In order to examine whether the in vivo administration of the fractions of the Seoritae, field bean, Seomoktae and soybean extracts shows inhibitory effects on thrombosis, the following test was carried out. On male SD (Sprague Dawley) rats weighing 220-250 g, a test for venous thrombosis was performed.

A solution of 200 mg of each fraction in saline was administered to SD rats at a dose of 10 ml/kg. At 1 hour after administration of the fraction, the rats were anesthetized by intra-abdominal administration of 12.5 g/kg of urethane, and the abdomen was open, and adipose tissue was removed so that the caudal vena cava was exposed. The adipose tissue was carefully removed in such a manner that the surrounding blood vessels would not be damaged. Filter paper (2 mm×4 mm) wetted with 3 µl of 5% $FeCl_3$ solution was applied onto the caudal vena cava for 5 minutes, and then removed. After 30 minutes, the caudal vena cava containing thrombus was ligated to a length of 12 mm and excised. The thrombus mass was placed in saline and dewatered, and the weight thereof was measured. The results of the measurement are shown in FIG. 2.

Figure 2:
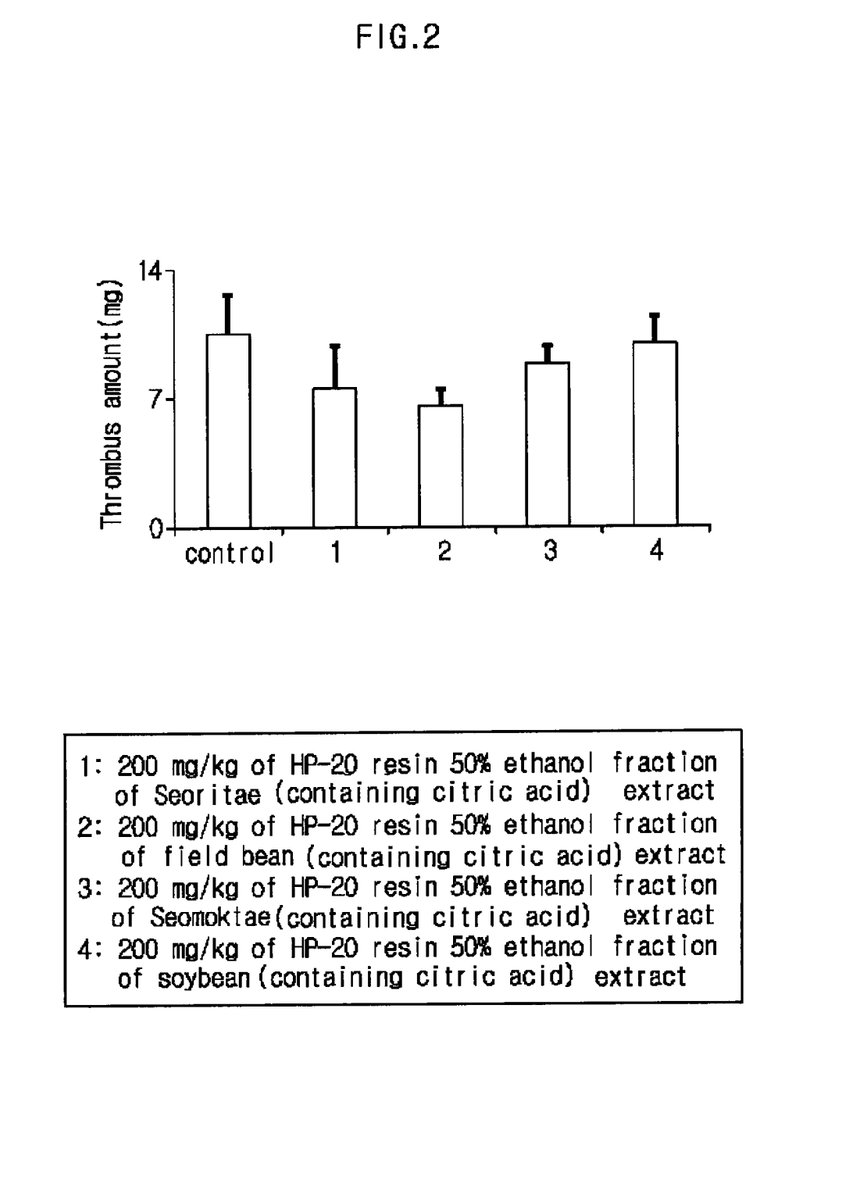
FIG. 2 is a graph showing the thrombosis inhibitory effects of oral administration of 50% ethanol fractions obtained by fractionating 20% ethanol organic acid extracts of various beans with HP-20 resin.

As can be seen in FIG. 2, the HP-20 resin ethanol fractions of Seoritae and field beans significantly inhibited thrombosis when administered orally at a dose of 200 mg/kg.

Figure 3:
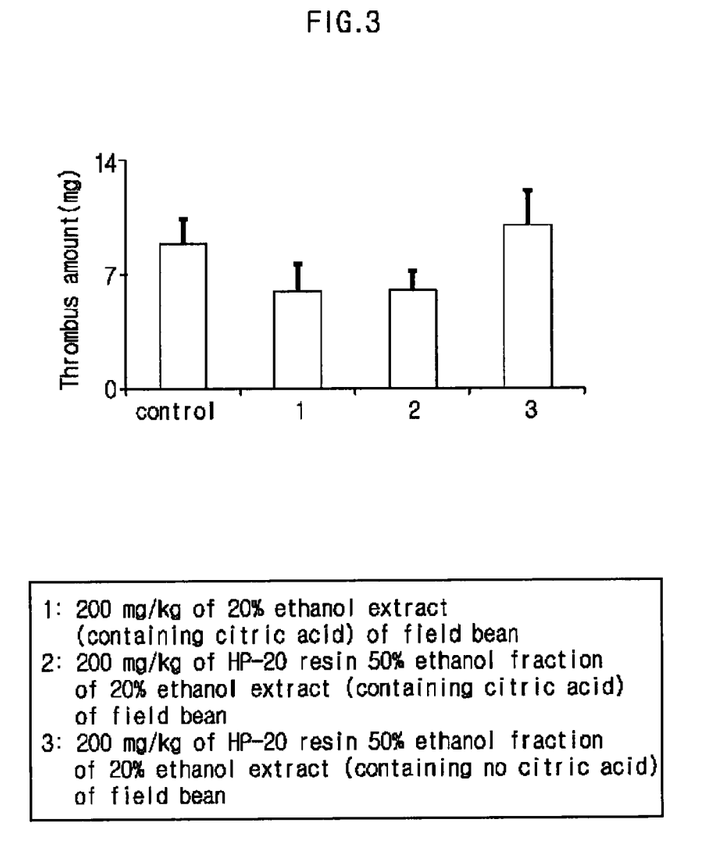
FIG. 3 is a graph showing the thrombosis inhibitory effects of oral administration of a 20% ethanol organic acid extract, a HP-20 resin 50% ethanol fraction of the extract and a HP-20 resin 50% ethanol fraction of a field bean extract obtained without using an organic acid.

In the same manner as above, the 20% ethanol organic acid extract of field beans, the HP-20 resin 50% ethanol fraction of the extract, and the HP-20 resin 50% ethanol fraction of a field bean extract obtained without using an organic acid were tested. The results of the test are shown in FIG. 3. As can be seen in FIG. 3, the 20% ethanol organic acid extract of the field bean extract and the HP-20 resin 50% ethanol fraction of the extract significantly thrombosis when administered orally at a dose of 200 mg/kg.

Figure 4:
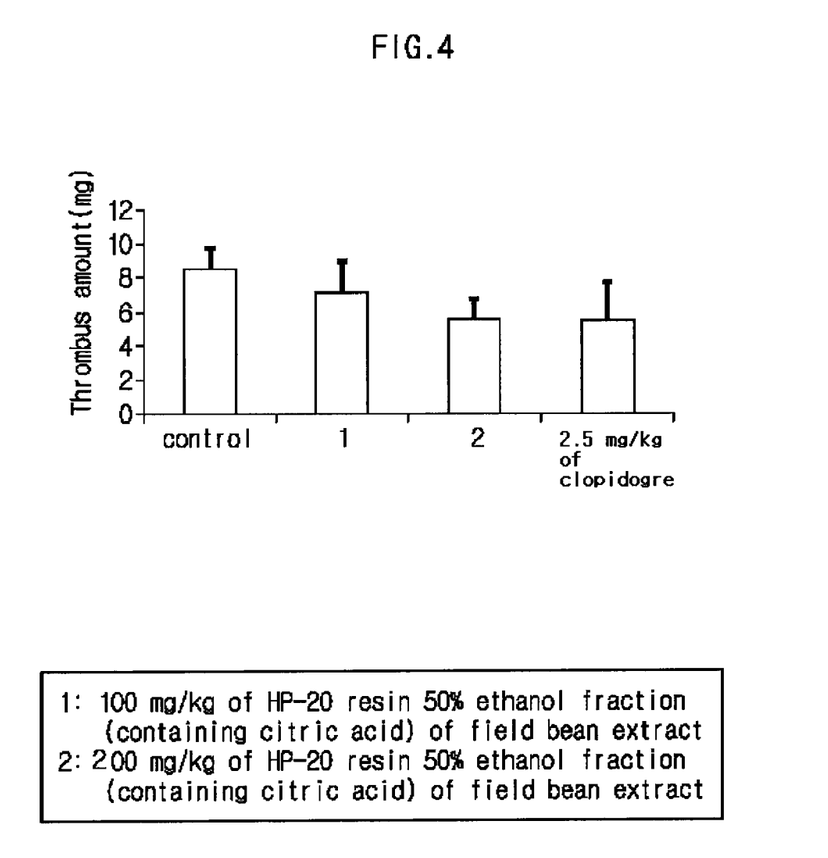
FIG. 4 is a graph showing the thrombosis inhibitory effect of a 50% ethanol fraction, obtained by fractionating a 20% ethanol containing organic acid extract of field beans with HP-20 resin, as a function of the dose of the ethanol fraction.

Finally, in the same manner as above, a test was performed for 100 and 200 mg/kg of the HP-20 resin 50% ethanol fraction of the 20% ethanol extract of field beans, and 2.5 mg/kg of the commercially available antithrombotic agent clopidogrel. A solvent (not containing the active ingredient) was used as a negative control. The results of the test are shown in FIG. 4. As can be seen in FIG. 4, the HP-20 resin 50% ethanol fraction of the 20% ethanol extract of field beans inhibited thrombosis in a concentration-dependent manner as compared to the negative control. Among them, 200 mg/kg of the HP-20 resin 50% ethanol fraction of the 20% ethanol extract of field beans showed an effect similar to that of 2.5 mg/kg of clopidogrel. Thus, it can be seen that the HP-20 resin 50% ethanol fraction of the field bean extract acts as an excellent antithrombotic agent.

Test Example 9

Observation of Inhibitory Effects on Aggregation of Platelets Isolated From SD Rats In order to examine whether the HP-20 resin 50% ethanol fraction of the field bean extract, the butanol fraction of the field bean extract, and the HP-20 resin 50% ethanol fraction of the extract of soybeans (frequently used as foods), have inhibitory effects on the aggregation of platelets isolated from rat, a test was performed using 15 µg/ml of collagen in the same manner as Test Example 1. The each bean fraction was used at a concentration of 400 µg/ml. The results of the test are expressed in Table 8 below as platelet aggregation inhibitory rates (%).

TABLE 8

|  | Inhibition rate (%) |
|---|---|
| Soybean | 96 |
| Field bean | 98 |
| Butanol fraction of field bean | 98 |

As can be seen in Table 8 below, the HP-20 resin 50% ethanol fraction of the field bean extract, the butanol fraction of the field bean extract, and the HP-20 resin 50% ethanol fraction of the soybean extract all showed excellent inhibitory effects on platelet aggregation in rats.

The invention claimed is:

1. A method for inhibiting thrombosis, the method comprising administering an effective amount of a resin fraction of a field bean extract to a subject in need thereof, wherein the field bean extract is obtained by extracting the field bean with a mixture of ethanol and an organic acid, and wherein the resin fraction is a fraction obtained by fractionation of the field bean extract with a synthetic adsorbent column that includes a polymer of benzene and polystyrene.

2. The method of claim 1, wherein the resin fraction is a fraction obtained by fractionating the field bean extract with butanol.

3. The method of claim 1, wherein the organic acid is any one of more selected from the group consisting of citric acid, acetic acid, butyric acid, palmitic acid, oxalic acid, tartaric acid, carboxylic acid and sulfonic acid.

4. The method of claim 1, wherein the ethanol is 1-40% (v/v) ethanol.

5. The method of claim 1, wherein the ethanol is 5-25% (v/v) ethanol.

* * * * *